United States Patent
Schulz

(10) Patent No.: US 9,730,444 B2
(45) Date of Patent: *Aug. 15, 2017

(54) HERBICIDAL COMPOSITIONS COMPRISING ISOXABEN AND AMINOPYRALID

(71) Applicant: Dow AgroSciences LLC, Indianapolis, IN (US)

(72) Inventor: Thomas Schulz, Niederschoena (DE)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/201,430

(22) Filed: Mar. 7, 2014

(65) Prior Publication Data

US 2014/0256550 A1 Sep. 11, 2014

Related U.S. Application Data

(60) Provisional application No. 61/775,031, filed on Mar. 8, 2013.

(51) Int. Cl.
| | | |
|---|---|---|
| *A01N 43/80* | (2006.01) | |
| *A01N 43/40* | (2006.01) | |
| *A01N 43/82* | (2006.01) | |

(52) U.S. Cl.
CPC .............. *A01N 43/40* (2013.01); *A01N 43/80* (2013.01)

(58) Field of Classification Search
CPC ......... A01N 43/80; A01N 43/40; A01N 43/82
See application file for complete search history.

(56) References Cited

U.S. PATENT DOCUMENTS

| | | | |
|---|---|---|---|
| 4,636,243 A * | 1/1987 | Burow, Jr. | 504/271 |
| 6,297,197 B1 * | 10/2001 | Fields et al. | 504/260 |
| 2006/0211576 A1 | 9/2006 | Zagar et al. | |
| 2008/0242546 A1 | 10/2008 | Schultz et al. | |
| 2009/0062121 A1 | 3/2009 | Satchivi et al. | |
| 2010/0048397 A1 | 2/2010 | Lewis | |
| 2011/0118119 A1 | 5/2011 | Spesard et al. | |
| 2011/0190130 A1 | 8/2011 | Garzon | |

FOREIGN PATENT DOCUMENTS

| | | | |
|---|---|---|---|
| JP | 2010-163411 | * | 7/2010 |
| WO | 94/07368 A1 | | 4/1994 |
| WO | 2010066679 A2 | | 6/2010 |

OTHER PUBLICATIONS

Machine translation of WO 2010/066679 (Jun. 2010).*
Machine translation of JP 2010-163411 (Jul. 2010).*
CABA abstract 1984:103705 (1984).*
IP 88909D, disclosed anonymously, Mar. 4, 2005.*
Derwent abstract 2010-J62154, abstracting JP 2010-163411 (Jul. 29, 2010).*
Extended European Search Report issued by the European Patent Office for PCT/US2014/021679 issued Jul. 5, 2016.
Richer, Synergism—A Patent View, Society of Chemical Industry, p. 309-315, 1987.

* cited by examiner

*Primary Examiner* — John Pak
(74) *Attorney, Agent, or Firm* — Michael R. Asam; Meunier Carlin Curfman, LLC

(57) ABSTRACT

Herbicidal compositions and methods of controlling undesirable vegetation using a combination of (a) isoxaben, (b) aminopyralid or an agriculturally acceptable salt or ester thereof, and optionally (c) flufenacet and (d) diflufenacet provide control of broad-leaved weeds.

15 Claims, No Drawings

HERBICIDAL COMPOSITIONS COMPRISING ISOXABEN AND AMINOPYRALID

CROSS-REFERENCE TO RELATED APPLICATIONS

This application claims the benefit of U.S. Provisional Patent Application Ser. No. 61/775,031 filed Mar. 8, 2013, the disclosure of which is expressly incorporated herein by reference.

BACKGROUND

The protection of crops from weeds and other vegetation which inhibit crop growth is a constantly recurring problem in agriculture. To help combat this problem, researchers in the field of synthetic chemistry have produced an extensive variety of chemicals and chemical formulations effective in the control of such unwanted growth. Chemical herbicides of many types have been disclosed in the literature and a large number are in commercial use. However, there remains a need for compositions and methods that are effective in controlling undesirable vegetation.

SUMMARY

Provided herein are herbicidal compositions comprising (a) isoxaben, (b) aminopyralid or an agriculturally acceptable salt or ester thereof, and optionally flufenacet and diflufenican.

Also provided are methods of controlling broadleaved weeds comprising applying a herbicidally effective amount of a combination comprising (a) isoxaben, (b) aminopyralid or an agriculturally acceptable salt or ester thereof, and optionally flufenacet and diflufenican.

DETAILED DESCRIPTION

Definitions

Isoxaben is the common name for N-[3-(1-ethyl-1-methylpropyl)isoxazol-5-yl]-2,6-dimethoxybenzamide. As described in Tomlin, C. D. S., Ed. *The Pesticide Manual: A World Compendium,* 15$^{th}$ ed.; BCPC: Alton, 2009 (hereafter "The Pesticide Manual"), isoxaben is a selective herbicide that inhibits cell wall biosynthesis. It is used, for example, pre-emergence in winter and spring cereals.

Aminopyralid is the common name for 4-amino-3,6-dichloropyridine-2-carboxylic acid. As described in *The Pesticide Manual*, aminopyralid is a synthetic auxin used in combination with fluoroxypyr for long-term control of annual and perennial broad-leaved weeds in grassland. *The Pesticide Manual* specifically identifies the salt aminopyralid-triisopropanolammonium.

Flufenacet is the common name for N-(4-fluorophenyl)-N-(1-methylethyl)-2-[[5-(trifluoromethyl)-1,3,4-thiadiazol-2-yl]oxy]acetamide. As described in *The Pesticide Manual*, flufenacet is a systemic herbicide for which the target site may be fatty acid metabolism. It is used, for example, post-emergence in maize, wheat, and rice.

Diflufenican is the common name for N-(2,4-difluorophenyl)-2-[3-(trifluormethyl)phenoxy]-3-pyridinecarboxamide. As described in *The Pesticide Manual*, diflufenican is a selective contact and residual herbicide that blocks carotenoid biosynthesis. It is used pre- and early post-emergence in autumn-sown wheat and barley to control grass and broad-leaved weeds. It is typically used in combination with other cereal herbicides, e.g. flufenacet.

As used herein, control of or controlling undesirable vegetation means killing or preventing the vegetation, or causing some other adversely modifying effect to the vegetation e.g., deviations from natural growth or development, regulation, desiccation, retardation, and the like.

As used herein, herbicide and herbicidal active ingredient mean a compound that controls undesirable vegetation when applied in an appropriate amount.

As used herein, a herbicidally effective or vegetation controlling amount is an amount of herbicidal active ingredient the application of which controls the relevant undesirable vegetation.

As used herein, applying an herbicide or herbicidal composition means delivering it directly to the targeted vegetation or to the locus thereof or to the area where control of undesired vegetation is desired. Methods of application include, but are not limited to pre-emergence, post-emergence, foliar, soil, and in-water applications. Described herein are methods of controlling undesirable vegetation by applying certain herbicide combinations or compositions.

As used herein, plants and vegetation include, but are not limited to, dormant seeds, germinant seeds, emerging seedlings, plants emerging from vegetative propagules, immature vegetation, and established vegetation.

As used herein, agriculturally acceptable salts and esters refer to salts and esters that exhibit herbicidal activity, or that are or can be converted in plants, water, or soil to the referenced herbicide. Exemplary agriculturally acceptable esters are those that are or can by hydrolyzed, oxidized, metabolized, or otherwise converted, e.g., in plants, water, or soil, to the corresponding carboxylic acid which, depending upon the pH, may be in the dissociated or undissociated form.

Exemplary salts include those derived from alkali or alkaline earth metals and those derived from ammonia and amines. Exemplary cations include sodium, potassium, magnesium, and ammonium cations of the formula:

$$R^1R^2R^3R^4N^+$$

wherein $R^1$, $R^2$, $R^3$ and $R^4$ each, independently represents hydrogen or $C_1$-$C_{12}$ alkyl, $C_3$-$C_{12}$ alkenyl or $C_3$-$C_{12}$ alkynyl, each of which is optionally substituted by one or more hydroxy, $C_1$-$C_4$ alkoxy, $C_1$-$C_4$ alkylthio or phenyl groups, provided that $R^1$, $R^2$, $R^3$ and $R^4$ are sterically compatible. Additionally, any two of $R^1$, $R^2$, $R^3$ and $R^4$ together may represent an aliphatic difunctional moiety containing one to twelve carbon atoms and up to two oxygen or sulfur atoms. Salts can be prepared by treatment with a metal hydroxide, such as sodium hydroxide, with an amine, such as ammonia, trimethylamine, diethanolamine, 2-methylthiopropylamine, bisallylamine, 2-butoxyethylamine, morpholine, cyclododecylamine, or benzylamine or with a tetraalkylammonium hydroxide, such as tetramethylammonium hydroxide or choline hydroxide.

Exemplary esters include those derived from $C_1$-$C_{12}$ alkyl, $C_3$-$C_{12}$ alkenyl, $C_3$-$C_{12}$ alkynyl or $C_7$-$C_{10}$ aryl-substituted alkyl alcohols, such as methyl alcohol, isopropyl alcohol, 1-butanol, 2-ethylhexanol, butoxyethanol, methoxypropanol, allyl alcohol, propargyl alcohol, cyclohexanol or unsubstituted or substituted benzyl alcohols. Benzyl alcohols may be substituted with from 1-3 substituents independently selected from halogen, $C_1$-$C_4$ alkyl or $C_1$-$C_4$ alkoxy. Esters can be prepared by coupling of the acids with the alcohol using any number of suitable activating agents such as those used for peptide couplings such as dicyclohexylcarbodiimide (DCC) or carbonyl diimidazole (CDI); by reacting the acids with alkylating agents such as alkylhalides or alkylsulfonates in the presence of a base such as triethylamine or lithium carbonate; by reacting the corresponding acid chloride of an acid with an appropriate alcohol; by reacting the corresponding acid with an appropriate alcohol in the presence of an acid catalyst or by transesterification.

As used herein, weight ratios of mixtures are calculated using the acid equivalent weight(s) of any compounds in the mixture that are salts or esters.

Compositions and Methods

Provided herein are herbicidal compositions comprising (a) isoxaben and (b) aminopyralid or an agriculturally acceptable salt or ester thereof, wherein the weight ratio of active ingredients is in the range of about 20-80 of (a) to about 2.5-10 of (b). In certain embodiments the weight ratio of (a) to (b) is from 0.5 to 32. In some embodiments the herbicidal active ingredients in the composition consist of isoxaben and aminopyralid or an agriculturally acceptable salt or ester thereof, i.e., these are the only herbicidally active ingredients in the composition.

In certain embodiments the herbicidal composition comprises (a) isoxaben, (b) aminopyralid or an agriculturally acceptable salt or ester thereof, and (c) flufenacet, wherein the weight ratio of active ingredients is in the range 20-80 of (a) to about 2.5-10 of (b) to about 100-600 of (c). In certain embodiments the weight ratio of (a) to (b) is from 0.5 to 32, and the weight ratio of (a) to (c) is from 0.05 to 0.80. In some embodiments the herbicidal active ingredients in the composition consist of isoxaben, aminopyralid or an agriculturally acceptable salt or ester thereof, and flufenacet.

In certain embodiments the herbicidal composition comprises (a) isoxaben, (b) aminopyralid or an agriculturally acceptable salt or ester thereof, (c) flufenacet, and (d) diflufenican wherein the weight ratio of active ingredients is in the range 20-80 of (a) to about 2.5-10 of (b) to about 100-600 of (c) to about 50-200 of (d). In certain embodiments the weight ratio of (a) to (b) is from 0.5 to 32, the weight ratio of (a) to (c) is from 0.03 to 0.80, and the weight ratio of (a) to (d) is from 0.1 to 1.6. In some embodiments the herbicidal active ingredients in the composition consist of isoxaben, aminopyralid or an agriculturally acceptable salt or ester thereof, flufenacet, and diflufenican.

The compositions may also contain an agriculturally acceptable adjuvant or carrier.

Also provided are methods of controlling broadleaved weeds comprising applying one of the above described compositions to the locus where control is desired.

Furthermore, in some embodiments, the combination of (a) isoxaben and (b) aminopyralid or an agriculturally acceptable salt or ester thereof, or the combination of (a) isoxaben, (b) aminopyralid or an agriculturally acceptable salt or ester thereof, and (c) flufenacet, or the combination of (a) isoxaben, (b) aminopyralid or an agriculturally acceptable salt or ester thereof, (c) flufenacet, and (d) diflufenican exhibits synergism, i.e., the herbicidal active ingredients are more effective in combination than when applied individually. The *Herbicide Handbook* of the Weed Science Society of America, Ninth Edition, 2007, p. 429 notes that synergism is "an interaction of two or more factors such that the effect when combined is greater than the predicted effect based on the response of each factor applied separately." In certain embodiments, the compositions exhibit synergy as determined by the Colby's equation. Colby, S. R. Calculation of the synergistic and antagonistic response of herbicide combinations. *Weeds* 1967, 15, 20-22.

Herbicidal activity (control of undesirable vegetation) is exhibited by the compositions when they are applied directly to the plant or to the locus of the plant at any stage of growth. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted to promote non-selective or selective herbicidal action. In some embodiments, the compositions described herein are applied to relatively immature undesirable vegetation to achieve the maximum control of weeds.

In some embodiments, the compositions and methods provided herein are utilized to control weeds in cereal crops, including but not limited to rice, wheat, barley, tritcale, oats, rye, sorghum, corn/maize, and also in cereal crops that are tolerant to glyphosate, glufosinate, dicamba, imidazolinone, phenoxy auxin, pyridyloxy auxin, aryloxyphenoxypropionate, acetyl CoA carboxylase (ACCase), acetolactate synthase (ALS), 4-hydroxyphenyl-pyruvate dioxygenase (HPPD), protoporphyrinogen oxidase (PPO), triazine, or bromoxynil.

In some embodiments, the compositions and methods provided herein are utilized to control undesirable vegetation consisting of broadleaf weeds.

In some embodiments, the compositions and methods provided herein are utilized to control undesirable vegetation such as chickweed (*Stellaria media* (L.) Vill), and geranium (*Geranium dissectum* L.).

The application rate will depend upon the particular type of weed to be controlled, the degree of control required, and the timing and method of application. In some embodiments, the composition is applied at an application rate of from about 22.5 grams active ingredient per hectare (g ai/ha) to about 890 g ai/ha based on the total amount of active ingredients in the composition. In certain embodiments, the composition is applied at an application rate of from about 35 g ai/ha to about 350 g ai/ha based on the total amount of active ingredients in the composition.

In some embodiments, the isoxaben is applied at a rate from about 20 g ai/ha to about 80 g ai/ha and aminopyralid or an agriculturally acceptable salt or ester thereof is applied at a rate of from about 2.5 to about 10 grams acid equivalent per hectare (g ae/ha). In some embodiments, the isoxaben is applied at a rate of about 40 g ai/ha and aminopyralid or an agriculturally acceptable salt or ester thereof is applied at a rate of about 5 g ae/ha.

In some embodiments, the isoxaben is applied at a rate from about 20 g ai/ha to about 80 g ai/ha, the aminopyralid or an agriculturally acceptable salt or ester thereof is applied at a rate of from 2.5 to 10 g ae/ha, and the flufenacet is applied at a rate from about 100 g ai/ha to about 600 g ai/ha. In some embodiments, the isoxaben is applied at a rate of about 40 g ai/ha, the aminopyralid or an agriculturally acceptable salt or ester thereof is applied at a rate of about 5 g ae/ha, and the flufenacet is applied at a rate of about 200 g ai/ha.

In some embodiments, the isoxaben is applied at a rate from about 20 g ai/ha to about 80 g ai/ha, the aminopyralid or an agriculturally acceptable salt or ester thereof is applied at a rate of from 2.5 to 10 g ae/ha, the flufenacet is applied at a rate from about 100 g ai/ha to about 600 g ai/ha, and the diflufenican is applied at a rate of from about 50 g ai/ha to about 200 g ai/ha. In some embodiments, the isoxaben is applied at a rate of about 40 g ai/ha, the aminopyralid or an agriculturally acceptable salt or ester thereof is applied at a rate of about 5 g ae/ha, the flufenacet is applied at a rate from about 200 g ai/ha, and the diflufenican is applied at a rate of about 100 g ai/ha.

In some embodiments, the isoxaben is applied at a rate of about 40 g ai/ha and the flufenacet is applied at a rate of about 200 g ai/ha. In some embodiments, the isoxaben is applied at a rate from about 20 g ai/ha to about 80 g ai/ha and the flufenacet is applied at a rate from about 100 g ai/ha to about 600 g ai/ha, and the diflufenican is applied at a rate of about 50-200 g ai/ha. In some embodiments, the isoxaben is applied at a rate of about 40 g ai/ha, the flufenacet is applied at a rate of about 200 g ai/ha, and the diflufenican is applied at a rate of about 100 g ai/ha.

The components of the mixtures described herein can be applied either separately or as part of a multipart herbicidal system. In some embodiments of the methods described herein, the active ingredients are applied simultaneously, including, e.g., in the form of a composition. In some embodiments, the active ingredients are applied sequentially, e.g., within 5, 10, 15, or 30 minutes of each other; 1, 2, 3, 4, 5, 10, 12, 24, 48 hour(s) of each other, or 1 week of each other.

The mixtures described herein can be applied in conjunction with one or more other herbicides to control a wider variety of undesirable vegetation. When used in conjunction with other herbicides, the composition can be formulated with the other herbicide or herbicides, tank-mixed with the other herbicide or herbicides or applied sequentially with the other herbicide or herbicides. Some of the herbicides that can be employed in conjunction with the compositions and methods described herein include, but are not limited to: 4-CPA, 4-CPB, 4-CPP, 2,4-D, 2,4-D choline salt, 2,4-D esters and amines, 2,4-DB, 3,4-DA, 3,4-DB, 2,4-DEB, 2,4-DEP, 3,4-DP, 2,3,6-TBA, 2,4,5-T, 2,4,5-TB, acetochlor, acifluorfen, aclonifen, acrolein, alachlor, allidochlor, alloxydim, allyl alcohol, alorac, ametridione, ametryn, amibuzin, amicarbazone, amidosulfuron, aminocyclopyrachlor, amiprofos-methyl, amitrole, ammonium sulfamate, anilofos, anisuron, asulam, atraton, atrazine, azafenidin, azimsulfuron, aziprotryne, barban, BCPC, beflubutamid, benazolin, bencarbazone, benfluralin, benfuresate, bensulfuron-methyl, bensulide, benthiocarb, bentazon-sodium, benzadox, benzfendizone, benzipram, benzobicyclon, benzofenap, benzofluor, benzoylprop, benzthiazuron, bicyclopyrone, bifenox, bilanafos, bispyribac-sodium, borax, bromacil, bromobonil, bromobutide, bromofenoxim, bromoxynil, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole, chlorprocarb, carfentrazone-ethyl, CDEA, CEPC, chlomethoxyfen, chloramben, chloranocryl, chlorazifop, chlorazine, chlorbromuron, chlorbufam, chloreturon, chlorfenac, chlorfenprop, chlorflurazole, chlorflurenol, chloridazon, chlorimuron, chlornitrofen, chloropon, chlorotoluron, chloroxuron, chloroxynil, chlorpropham, chlorsulfuron, chlorthal, chlorthiamid, cinidon-ethyl, cinmethylin, cinosulfuron, cisanilide, clethodim, cliodinate, clodinafop-propargyl, clofop, clomazone, clomeprop, cloprop, cloproxydim, clopyralid, cloransulam-methyl, CMA, copper sulfate, CPMF, CPPC, credazine, cresol, cumyluron, cyanatryn, cyanazine, cycloate, cyclosulfamuron, cycloxydim, cycluron, cyhalofop-butyl, cyperquat, cyprazine, cyprazole, cypromid, daimuron, dalapon, dazomet, delachlor, desmedipham, desmetryn, di-allate, dicamba, dichlobenil, dichloralurea, dichlormate, dichlorprop, dichlorprop-P, diclofop-methyl, diclosulam, diethamquat, diethatyl, difenopenten, difenoxuron, difenzoquat, diflufenzopyr, dimefuron, dimepiperate, dimethachlor, dimethametryn, dimethenamid, dimethenamid-P, dimexano, dimidazon, dinitramine, dinofenate, dinoprop, dinosam, dinoseb, dinoterb, diphenamid, dipropetryn, diquat, disul, dithiopyr, diuron, DMPA, DNOC, DSMA, EBEP, eglinazine, endothal, epronaz, EPTC, erbon, esprocarb, ethalfluralin, ethbenzamide, ethametsulfuron, ethidimuron, ethiolate, ethobenzamid, etobenzamid, ethofumesate, ethoxyfen, ethoxysulfuron, etinofen, etnipromid, etobenzanid, EXD, fenasulam, fenoprop, fenoxaprop, fenoxaprop-P-ethyl, fenoxaprop-P-ethyl+ isoxadifen-ethyl, fenoxasulfone, fenteracol, fenthiaprop, fentrazamide, fenuron, ferrous sulfate, flamprop, flamprop-M, flazasulfuron, florasulam, fluazifop, fluazifop-P-butyl, fluazolate, flucarbazone, flucetosulfuron, fluchloralin, flufenican, flufenpyr-ethyl, flumetsulam, flumezin, flumiclorac-pentyl, flumioxazin, flumipropyn, fluometuron, fluorodifen, fluoroglycofen, fluoromidine, fluoronitrofen, fluothiuron, flupoxam, flupropacil, flupropanate, flupyrsulfuron, fluridone, fluorochloridone, fluoroxypyr, flurtamone, fluthiacet, fomesafen, foramsulfuron, fosamine, fumiclorac, furyloxyfen, glufosinate, glufosinate-ammonium, glufosinate-P-ammonium, glyphosate, halosafen, halosulfuron-methyl, haloxydine, haloxyfop-methyl, haloxyfop-P-methyl, hexachloroacetone, hexaflurate, hexazinone, imazamethabenz, imazamox, imazapic, imazapyr, imazaquin, imazosulfuron, imazethapyr, indanofan, indaziflam, iodobonil, iodomethane, iodosulfuron, iodosulfuron-ethyl-sodium, iofensulfuron, ioxynil, ipazine, ipfencarbazone, iprymidam, isocarbamid, isocil, isomethiozin, isonoruron, isopolinate, isopropalin, isoproturon, isouron, isoxaben, isoxachlortole, isoxaflutole, isoxapyrifop, karbutilate, ketospiradox, lactofen, lenacil, linuron, MAA, MAMA, MCPB, mecoprop, mecoprop-P, medinoterb, mefenacet, mefluidide, mesoprazine, mesosulfuron, mesotrione, metam, metamifop, metamitron, metazachlor, metazosulfuron, metflurazon, methabenzthiazuron, methalpropalin, methazole, methiobencarb, methiozolin, methiuron, methometon, methoprotryne, methyl bromide, methyl isothiocyanate, methyldymron, metobenzuron, metobromuron, metolachlor, metosulam, metoxuron, metribuzin, metsulfuron, metsulfuron-methyl, molinate, monalide, monisouron, monochloroacetic acid, monolinuron, monuron, morfamquat, MSMA, naproanilide, napropamide, naptalam, neburon, nicosulfuron, nipyraclofen, nitralin, nitrofen, nitrofluorfen, norflurazon, noruron, OCH, orbencarb, ortho-dichlorobenzene, orthosulfamuron, oryzalin, oxadiargyl, oxadiazon, oxapyrazon, oxasulfuron, oxaziclomefone, oxyfluorfen, paraflufen-ethyl, parafluoron, paraquat, pebulate, pelargonic acid, pendimethalin, penoxsulam, pentachlorophenol, pentanochlor, pentoxazone, perfluidone, pethoxamid, phenisopham, phenmedipham, phenmedipham-ethyl, phenobenzuron, phenylmercury acetate, picloram, picolinafen, pinoxaden, piperophos, potassium arsenite, potassium azide, potassium cyanate, pretilachlor, primisulfuron-methyl, procyazine, prodiamine, profluazol, profluralin, profoxydim, proglinazine, prohexadione-calcium, prometon, prometryn, pronamide, propachlor, propanil, propaquizafop, propazine, propham, propisochlor, propoxycarbazone, propyrisulfuron, propyzamide, prosulfalin, prosulfocarb, prosulfuron, proxan, prynachlor, pydanon, pyraclonil, pyraflufen-ethyl, pyrasulfotole, pyrazogyl, pyrazolynate, pyrazosulfuron-ethyl, pyrazoxyfen, pyribenzoxim, pyributicarb, pyriclor, pyridafol, pyridate, pyriftalid, pyriminobac, pyrimisulfan, pyrithiobac-sodium, pyroxasulfone, pyroxsulam, quinclorac, quinmerac, quinoclamine, quinonamid, quizalofop, quizalofop-P-ethyl, rhodethanil, rimsulfuron, saflufenacil, S-metolachlor, sebuthylazine, secbumeton, sethoxydim, siduron, simazine, simeton, simetryn, SMA, sodium arsenite, sodium azide, sodium chlorate, sulcotrione, sulfallate, sulfentrazone, sulfometuron, sulfosate, sulfosulfuron, sulfuric acid, sulglycapin, swep, TCA, tebutam, tebuthiuron, tefuryltrione, tembotrione, tepraloxydim, terbacil, terbucarb, terbuchlor, terbumeton, terbuthylazine, terbutryn, tetrafluoron, thenylchlor, thiazafluoron, thiazopyr, thidiazimin, thidiazuron, thiencarbazone-methyl, thifensulfuron, thifensulfurn-methyl, thiobencarb, tiocarbazil, tioclorim, topramezone, tralkoxydim, triafamone, tri-allate, triasulfuron, triaziflam, tribenuron, tribenuron-methyl, tricamba, triclopyr choline salt, triclopyr esters and salts, tridiphane, trietazine, trifloxysulfuron, trifluralin, triflusulfuron, trifop, trifopsime, trihydroxytriazine, trimeturon, tripropindan, tritac, tritosulfuron, vernolate, xylachlor and salts, esters, optically active isomers and mixtures thereof.

The compositions and methods described herein, can, further, be used in conjunction with glyphosate, glufosinate, dicamba, phenoxy auxins, pyridyloxy auxins, aryloxyphenoxypropionates, acetyl CoA carboxylase (ACCase) inhibitors, imidazolinones, acetolactate synthase (ALS) inhibitors, 4-hydroxyphenyl-pyruvate dioxygenase (HPPD) inhibitors, protoporphyrinogen oxidase (PPO) inhibitors, triazines, and bromoxynil on crops that are tolerant thereto, and on crops possessing multiple or stacked traits conferring tolerance to multiple chemistries and/or multiple modes-of-action.

In some embodiments, compositions provided herein further comprise at least one agriculturally acceptable adjuvant or carrier. Suitable adjuvants or carriers should not be phytotoxic to valuable crops, particularly at the concentrations employed in applying the compositions for selective weed control in the presence of crops, and should not react chemically with herbicidal components or other composition ingredients. Such mixtures can be designed for application directly to weeds or their locus or can be concentrates or formulations that are normally diluted with additional carriers and adjuvants before application. They can be solids, such as, for example, dusts, granules, water-dispersible granules, or wettable powders, or liquids, such as, for example, emulsifiable concentrates, solutions, emulsions or suspensions. They can also be provided as a pre-mix or tank-mixed.

Suitable agricultural adjuvants and carriers include, but are not limited to, crop oil concentrate; nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+urea ammonium nitrate; emulsified methylated seed oil; tridecyl alcohol (synthetic) ethoxylate (8EO); tallow amine ethoxylate (15 EO); PEG (400) dioleate-99.

Liquid carriers that can be employed include water and organic solvents. The organic solvents include, but are not limited to, petroleum fractions or hydrocarbons such as mineral oil, aromatic solvents, paraffinic oils, and the like; vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tung oil and the like; esters of the above vegetable oils; esters of monoalcohols or dihydric, trihydric, or other lower polyalcohols (4-6 hydroxy containing), such as 2-ethyl hexyl stearate, n-butyl oleate, isopropyl myristate, propylene glycol dioleate, di-octyl succinate, di-butyl adipate, di-octyl phthalate and the like; esters of mono, di and polycarboxylic acids and the like. Specific organic solvents include, but are not limited to toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methyl alcohol, ethyl alcohol, isopropyl alcohol, amyl alcohol, ethylene glycol, propylene glycol, glycerine, N-methyl-2-pyrrolidinone, N,N-dimethyl alkylamides, dimethyl sulfoxide, liquid fertilizers and the like. In certain embodiments, water is the carrier for the dilution of concentrates.

Suitable solid carriers include but are not limited to talc, pyrophyllite clay, silica, attapulgus clay, kaolin clay, kieselguhr, chalk, diatomaceous earth, lime, calcium carbonate, bentonite clay, Fuller's earth, cottonseed hulls, wheat flour, soybean flour, pumice, wood flour, walnut shell flour, lignin, cellulose, and the like.

In some embodiments, the compositions described herein further comprise one or more surface-active agents. In some embodiments, such surface-active agents are employed in both solid and liquid compositions, and in certain embodiments those designed to be diluted with carrier before application. The surface-active agents can be anionic, cationic or nonionic in character and can be employed as emulsifying agents, wetting agents, suspending agents, or for other purposes. Surfactants which may also be used in the present formulations are described, inter alia, in "McCutcheon's Detergents and Emulsifiers Annual," MC Publishing Corp., Ridgewood, N.J., 1998 and in "Encyclopedia of Surfactants," Vol. I-III, Chemical Publishing Co., New York, 1980-81. Surface-active agents include, but are not limited to salts of alkyl sulfates, such as diethanolammonium lauryl sulfate; alkylarylsulfonate salts, such as calcium dodecylbenzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkylnaphthalene-sulfonate salts, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryl trimethylammonium chloride; poly-ethylene glycol esters of fatty acids, such as polyethylene glycol stearate; block copolymers of ethylene oxide and propylene oxide; salts of mono and dialkyl phosphate esters; vegetable or seed oils such as soybean oil, rapeseed/canola oil, olive oil, castor oil, sunflower seed oil, coconut oil, corn oil, cottonseed oil, linseed oil, palm oil, peanut oil, safflower oil, sesame oil, tung oil and the like; and esters of the above vegetable oils, and in certain embodiments, methyl esters.

In some embodiments, these materials, such as vegetable or seed oils and their esters, can be used interchangeably as an agricultural adjuvant, as a liquid carrier or as a surface active agent.

Other exemplary additives for use in the compositions provided herein include but are not limited to compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like. The compositions may also contain other compatible components, for example, other herbicides, plant growth regulators, fungicides, insecticides, and the like and can be formulated with liquid fertilizers or solid, particulate fertilizer carriers such as ammonium nitrate, urea and the like.

In some embodiments, the concentration of the active ingredients in the compositions described herein is from 0.0005 to 98 percent by weight. In some embodiments, the concentration is from 0.0006 to 90 percent by weight. In compositions designed to be employed as concentrates, the active ingredients, in certain embodiments, are present in a concentration from 0.1 to 98 weight percent, and in certain embodiments, 0.5 to 90 weight percent. Such compositions are, in certain embodiments, diluted with an inert carrier, such as water, before application. The diluted compositions usually applied to weeds or the locus of weeds contain, in certain embodiments, 0.0006 to 3.0 weight percent active ingredient and in certain embodiments contain 0.01 to 0.3 weight percent.

The present compositions can be applied to weeds or their locus by the use of conventional ground or aerial dusters, sprayers, and granule applicators, by addition to irrigation or paddy water, and by other conventional means known to those skilled in the art.

The described embodiments and following examples are for illustrative purposes and are not intended to limit the scope of the claims. Other modifications, uses, or combinations with respect to the compositions described herein will be apparent to a person of ordinary skill in the art without departing from the spirit and scope of the claimed subject matter.

EXAMPLES

Results in Table 1 are for foliar-applied compositions in small plot research experiments to evaluate the efficacy of the compositions in winter wheat. Application water volume was 200 liters per hectare (L/ha). Crop stage at time of application was 12-13. Control of GERDI and STEME was evaluated visually (as percent (%) control) at intervals indicated in the table. The values reported are means. Means followed by the same letter in the table do not significantly differ (P=0.5, Duncan's New MRT). Colby's equation was used to determine the herbicidal effects expected from the mixtures (Colby, S. R. Calculation of the synergistic and antagonistic response of herbicide combinations. *Weeds* 1967, 15, 20-22.).

More specifically, the following equation is used to calculate the expected activity of mixtures containing two herbicical active ingredients:

$$\text{Expected} = A + B - (A \times B/100)$$

A=observed efficacy of a first active ingredient at the same concentration as used in the mixture;
B=observed efficacy of the second active ingredient (or product, which may contain a combination of active ingredients) at the same concentration as used in the mixture.

For mixtures containing three herbicidal active ingredients, the following equation was used to calculate the expected activity:

$$\text{Expected} = 100 - \frac{(100-A)(100-B)(100-C)}{10{,}000}$$

A=observed efficacy of a first active ingredient at the same concentration as used in the mixture;
B=observed efficacy of a second active ingredient B at the same concentration as used in the mixture;
C=observed efficacy of a third active ingredient C at the same concentration as used in the mixture.

The following abbreviations are used in Table 1:
GERDI=*Geranium dissectum* (cutleaf *geranium*)
STEME=*Stellaria media* (L.) Vill. (common chickweed)
g ai/ha=grams active ingredient per hectare
g ae/ha=grams acid equivalent per hectare
Ob=observed value of percent (%) control rated visually
Ex=expected value of percent (%) control as calculated by Colby's equation

TABLE 1

| Trial 1 | | | | | | | | | |
|---|---|---|---|---|---|---|---|---|---|
| | | | | | | | VISUAL % CONTROL OF STEME | | VISUAL % CONTROL OF GERDI |
| Treatment | | | | | | | | | |
| 1$^{st}$ active ingredient | | 2$^{nd}$ active ingredient | | 3$^{rd}$ active ingredient | | 28 DAT | | 28 DAT | |
| | | | | | | Ob | Ex | Ob | Ex |
| UNTREATED | | | | | | 0 e | | 0 d | |
| isoxaben | 40 g ai/ha | | | | | 0 e | | 0 d | |
| aminopyralid | 5 g ae/ha | | | | | 0 e | | 0 d | |
| flufenacet | 200 g ai/ha | | | | | 0 e | | 0 d | |
| flufenacet | 200 g ai/ha | diflufenican | 100 g ai/ha | | | 50 c | | 65 bc | |
| isoxaben | 40 g ai/ha | aminopyralid | 5 g ae/ha | | | 35 d | 0 | 53 c | 0 |
| isoxaben | 40 g ai/ha | aminopyralid | 5 g ae/ha | flufenacet | 200 g ai/ha | 79 a | 0 | 85 a | 0 |
| isoxaben | 40 g ai/ha | aminopyralid | 5 g ae/ha | flufenacet diflufenican | 200 g ai/ha 100 g ai/ha | 65 b | 50 | 89 a | 65 |

What is claimed is:

1. An herbicidal composition comprising (a) isoxaben and (b) aminopyralid or an agriculturally acceptable salt or ester thereof, wherein the weight ratio of (a) to (b) is 40:5.

2. The herbicidal composition of claim 1 wherein isoxaben and aminopyralid or an agriculturally acceptable salt or ester thereof are the only herbicidally active ingredients.

3. The herbicidal composition of claim 1 additionally comprising (c) flufenacet, wherein the weight ratio of (a) to (b) is 40:5:200.

4. The herbicidal composition of claim 3 wherein isoxaben, aminopyralid or an agriculturally acceptable salt or ester thereof, and flufenacet are the only herbicidally active ingredients.

5. The herbicidal composition of claim 1 additionally comprising (c) flufenacet, and (d) diflufenican, wherein the weight ratio of (a) to (b) to (c) to (d) is 40:5:200:100.

6. The herbicidal composition of claim 5 wherein isoxaben, aminopyralid or an agriculturally acceptable salt or ester thereof, flufenacet and diflufenican are the only herbicidally active ingredients.

7. A method of controlling undesirable vegetation which comprises applying to the an undesirable vegetation or locus thereof, an herbicidally effective amount of (a) isoxaben and (b) aminopyralid or an agriculturally acceptable salt or ester thereof, wherein the weight ratio of (a) to (b) is 40:5.

8. The method of claim 7 which further comprises applying an herbicidally effective amount of (c) flufenacet, wherein the weight ratio of (a) to (b) to (c) is 40:5:200.

9. The method of claim 8 wherein the application rate of (c) flufenacet is from 100 to 600 g ai/ha.

10. The method of claim 7 which further comprises applying an herbicidally effective amount of (c) flufenacet and (d) diflufenican, wherein the weight ratio of (a) to (b) to (c) to (d) is 40:5:200:100.

11. The method of claim 10 wherein the application rate of (d) diflufenican is from 50 to 200 g ai/ha.

12. The method of claim 7 wherein the application rate of (a) isoxaben is from 20 to 80 g ai/ha.

13. The method of claim 7, carried out in the presence of a cereal crop, wherein the cereal crop is rice, wheat, barley, triticale oats, rye, sorghum, or maize.

14. The method of claim 13 wherein the cereal crop is tolerant to glyphosate, glufosinate, dicamba, imidazolinone, phenoxy auxin, pyridyloxy auxin, aryloxyphenoxypropionate, acetyl CoA carboxylase (ACCase) inhibitors, acetolactate synthase (ALS) inhibitors, 4-hydroxyphenyl-pyruvate dioxygenase (HPPD) inhibitors, protoporphyrinogen oxidase (PPO) inhibitors, triazine, or bromoxynil.

15. The method of claim 7, wherein the undesirable vegetation comprises *Stellaria media* (L.) Vill, or *Geranium dissoctum L.*

* * * * *